United States Patent [19]
Campbell et al.

[11] Patent Number: 5,397,348
[45] Date of Patent: Mar. 14, 1995

[54] MECHANICAL HEART VALVE WITH COMPRESSIBLE STIFFENING RING

[75] Inventors: Louis A. Campbell; Joseph A. Sauter, both of Austin, Tex.

[73] Assignee: Carbomedics, Inc., Austin, Tex.

[21] Appl. No.: 166,252

[22] Filed: Dec. 13, 1993

[51] Int. Cl.6 ............................................. A61F 2/24
[52] U.S. Cl. ............................................. 623/2; 623/900
[58] Field of Search .................................. 623/2, 900

[56] References Cited

U.S. PATENT DOCUMENTS

| | | | |
|---|---|---|---|
| 3,744,060 | 7/1973 | Bellhouse et al. | 623/2 |
| 4,197,593 | 4/1980 | Kaster et al. | 623/2 |
| 4,535,483 | 8/1985 | Klawitter et al. | 623/2 |
| 4,666,442 | 5/1987 | Arru et al. | 623/2 |
| 4,790,843 | 12/1988 | Carpentier et al. | 623/2 |
| 4,863,460 | 9/1989 | Magladry | 623/2 |
| 5,035,709 | 7/1991 | Wieting et al. | 623/2 |
| 5,071,431 | 12/1991 | Sauter et al. | 623/2 |
| 5,104,406 | 4/1992 | Curcio et al. | 623/2 |
| 5,163,954 | 11/1992 | Curcio et al. | 623/2 |

*Primary Examiner*—David H. Willse
*Assistant Examiner*—Bruce E. Snow
*Attorney, Agent, or Firm*—John R. Merkling

[57] ABSTRACT

A prosthetic mechanical heart valve with an annular valve body and with a suture ring and stiffening ring combination wherein the stiffening ring is compressible before contacting a wall of the valve body. The inside diameter of the stiffening ring is consistently greater than the outside diameter of the annular valve body, forming a gap. This inhibits compressive forces from being transmitted to the annular valve body. The heart valve also has beveled stops or recesses for controlling the opening angle of leaflets mounted in the valve body. Because of the gap between the valve body and the stiffening ring, the body can deform in a spring-like manner, providing a spring-closing action.

28 Claims, 3 Drawing Sheets

MECHANICAL HEART VALVE WITH COMPRESSIBLE STIFFENING RING

BACKGROUND OF OUR INVENTION

Our invention is directed to a prosthetic mechanical heart valve with an improved stiffening ring, and in particular a stiffening ring which is compressible with respect to an annular body of the valve, whereby a satisfactory margin of safety is obtained despite a relatively thinner valve body and ring combination. This feature, coupled with beveled stops for valve leaflets, permits spring-loading of the leaflets, by deformation of the annular valve body.

Heart valve prostheses may be classified into two general categories: bioprosthetic heart valves and mechanical heart valves. By bioprosthetic heart valves we mean heart valves with generally flexible leaflets comprised of biological tissue. These include leaflets formed of treated human valve tissue (allografts), or of treated porcine or other non-human tissue (xenografts). By mechanical heart valves we mean heart valves comprised primarily of non-biologic materials, for example, metals, ceramics or polymers. These include ball valves and valves having one, two or more leaflets.

An implantable mechanical heart valve usually has an annular valve housing or body to provide a passageway for blood. Leaflets are mounted in the annular body and open or close the passageway. Usually there are one or two leaflets, but occasionally triple leaflet configurations have been proposed. On the outside of the valve body there is usually a circumferential groove. This groove is used to attach a suture ring to the valve body. The suture ring is used to sew the heart valve to the patient's heart tissue. A stiffening ring has been used with some sewing rings to give additional strength to the valve body. Generally, the stiffening ring has been designed to be in intimate contact with an outer surface of the valve body. An exception has been the CPHV (TM) heart valve made by Carbomedics, Inc., our assignee. Because this valve has been designed with a rotatable sewing ring, there has usually been a small gap of not more than 0.001 inch (0.025 mm) radially between the valve body and the stiffening ring. This has not, however, permitted a significant reduction in the radial thickness of the valve body and stiffening ring-/sewing ring combination with associated increase in orifice size.

SUMMARY OF OUR INVENTION

We have invented a prosthetic mechanical heart valve with an annular valve body and with a suture ring and stiffening ring combination wherein the stiffening ring is compressible before contacting a wall of the valve body. The inside diameter of the stiffening ring is consistently greater than the outside diameter of the annular valve body, forming a relatively substantial gap. This inhibits compressive forces from being transmitted to the annular valve body. Measured radially, there should be a gap of at least 0.001 inch (0.025 mm) and preferably greater than at least 0.0015 inch (0.038 mm). Further, we have provided beveled stops for controlling the opening angle of leaflets mounted in the valve body. Because of the gap between the valve body and the stiffening ring, the body can deform in a spring-like manner. This allows the leaflets to open more fully under higher loads and provides a spring-closing action as well. To prevent the leaflets from falling out of the valve body, the gap between the valve body and the stiffening ring should be no more than 0.015 inch (0.381 mm) and preferably no more than 0.007 inch (0.178 mm), measured radially.

With the foregoing in mind, it is an object of our invention to provide a mechanical heart valve having improved over-all resistance to compression by using a compressible stiffening ring.

It is also an object of our invention to provide such a heart valve with a thinner diametrical profile to improve flow characteristics.

Another object of our invention is to provide a mechanical heart valve with a stiffening ring wherein the annular valve body can deform within said ring in response to hemodynamic loads.

A further object has been to provide a mechanical heart valve with leaflets and tapered stops for restraining the motion of the leaflets and converting the kinetic energy of opening the leaflets into potential energy stored in the deformation of the annular body.

Other objects and advantages Of our invention will become apparent from the following detailed description, taken with reference to the accompanying drawings.

DETAILED DESCRIPTION OF OUR PREFERRED EMBODIMENT

Figure 1:
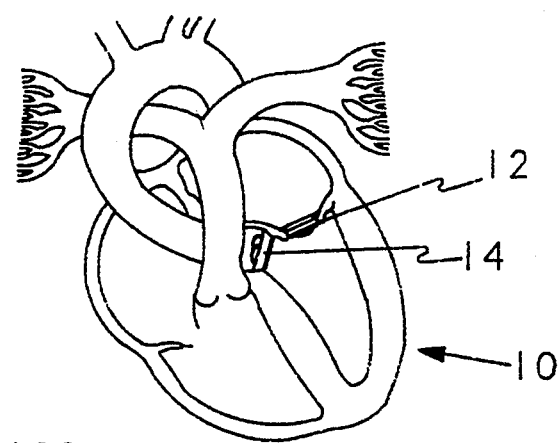
FIG. 1 is a cross-sectional view of a human heart, showing placement of a mitral prosthetic heart valve and an aortic prosthetic heart valve.

We will now describe our preferred embodiment of our invention with reference to the accompanying drawings. In the drawings, like numerals will designate like parts throughout.

FIG. 1 is a schematic through-section of the human heart 10 showing the placement of two mechanical heart valves. A mitral valve 12 is shown between the left atrium and the left ventricle of the heart. An aortic valve 14 is shown between the left ventricle and the ascending aorta. Blood flows from the atrium through the mitral valve 12 into the ventricle. The ventricle pumps blood through the aortic valve 14 to the body.

Figure 3:
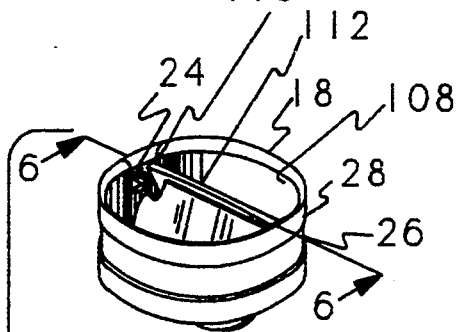
FIG. 3 is an exploded prospective view of the heart valve of FIG. 2.
Figure 3:
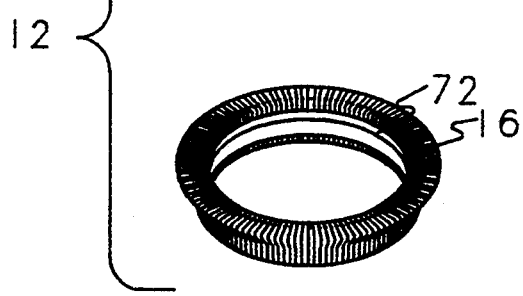
Figure 2:
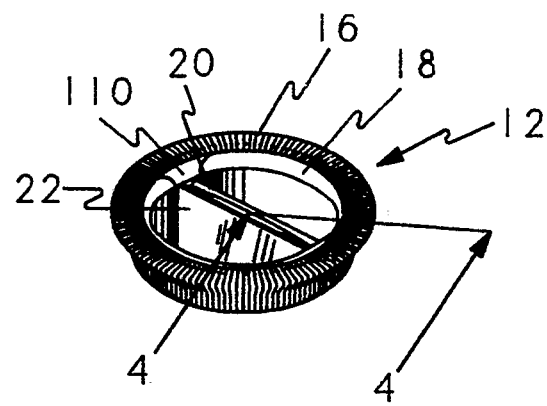
FIG. 2 is a prospective view of a prosthetic mechanical heart valve with a sewing ring.

FIG. 2 is a prospective view of the mitral prosthetic heart valve 12 with a suture ring 16 in accordance with our present invention. Although a mitral valve is particularly described, our invention is equally applicable to aortic valves. The heart valve 12 comprises an annular valve body 18 with pivoting leaflets 20, 22. In the embodiment shown, we have illustrated a bileaflet mechanical heart valve. Single leaflet and multiple leaflet valves could also be used without departing from the teachings of our invention. In FIG. 3, the leaflet 22 is shown with a portion cut away to reveal a recess 24. A mounting ear (shown in FIGS. 6 through 9) engages the recess 24, allowing the leaflet to pivot between open and closed positions. As shown FIG. 3, the annular valve body 18 has an exterior annular groove 26 on an outer surface 28 of the valve body. This groove 26 receives a stiffening ring 72, more particularly described below.

In our preferred embodiment, the annular valve body consists of pyrolitic carbon. Pyrolitic carbon is a hard, wear-resistant, biocompatible carbon, well suited for the construction of artificial heart valves. The material also has a relatively low Young's Modulus, on the order of 4,000,000 psi. An exterior stiffening ring such as the ring 72 is frequently used with a carbon valve body. The stiffening ring is comprised of a biocompatible metal such as cobalt-chromium, titanium, 6AL4V or $Al_2O$, which have a high Young's Modulus of 15,000,000 psi or greater.

Figure 4:
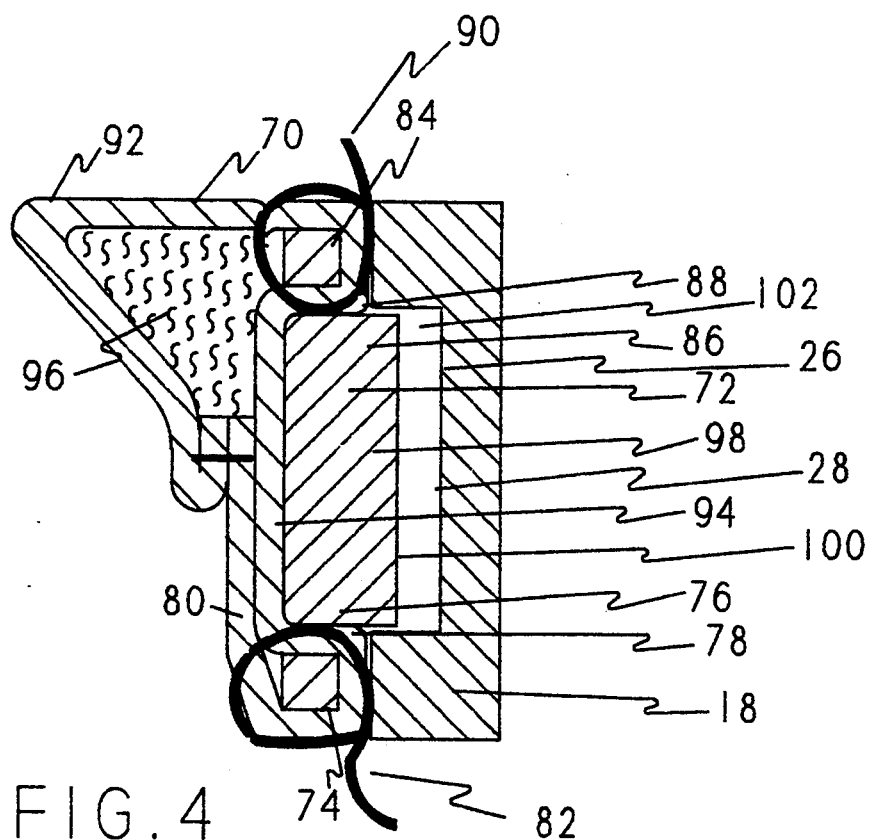
FIG. 4 is a cross-sectional view of a portion of the mechanical heart valve of FIG. 2, taken along line 4—4.

The construction of the suture ring can best be understood by reference to FIG. 4. The stiffening ring is attached to the valve body using a heat expansion technique before building the suture ring. Construction of the suture ring begins with a knit fabric tube 70. Polyester or PTFE fabric with a thickness of about 0.009 inches (0.20 mm) is a suitable material for such a tube. The tube 70 has a diameter approximating the outer diameter of the stiffening ring 72. The tube 70 is placed over the stiffening ring 72. A lower capture ring 74 is placed on the outside of the tube and pressed up against a lower edge 76 of the stiffening ring. This crimps the tube between the stiffening ring and the lower ring at a bend 78 as seen in FIG. 4. A lower end 80 of the tube is wrapped outwardly around the lower capture ring 74 and the ring is stitched in place. To sew the tube to the lower ring, a continuous suture 82 is passed around the ring. The suture preferably is passed in a clock-wise direction as seen in FIG. 4. The suture 82 passes between the stiffening ring 72 and the lower ring 74 through the bend 78 in the knit fabric.

After the lower ring 74 is sewn in place, an upper ring 84 is placed on the outside of the fabric tube and pressed down against an upper end 86 of the stiffening ring 72. As with the lower ring 74, this forms a bend 88 in the knit fabric, which bend is captured between the stiffening ring and the upper ring. Another continuous suture 90 is used to sew the upper ring in position. The suture 90 is passed completely around the upper ring 84 in a counter clock-wise direction as seen in FIG. 4. The stitches pass over the knit fabric in the region of the upper ring and between the upper ring 84 and the stiffening ring 72 through the bend 88. The upper and lower rings capture the stiffening ring between them. The relative thickness of the sewing ring is reduced because neither the tube nor the upper or lower ring pass beneath any portion of the stiffening ring. To complete the suture ring, an upper end 92 is folded down and the upper end 92 and the lower end 80 of the knit fabric are stitched to a center 94 of the knit fabric, circumferentially along the outside the stiffening ring. The upper end 92 flares away from the stiffening ring to provide a flange that can be sewn into the tissue at the implantation site. If desired, a filler 96 such as PTFE felt, or molded silicon may be captured within the upper end 92.

The stiffening ring 72 has an extended portion 98 which extends radially inward. The extended portion 98 extends radially inward farther than any other feature of the combination. The extended portion 98 fits into the groove 26 in the annular valve body 18 and has an interior cylindrical surface 100 which faces the bottom 28 of the groove 26. As with the embodiment shown in FIG. 4, the interior cylindrical surface 100 has a radial dimension measured across the valve body which is greater than the radial dimension of the bottom 28 of the groove 26. Consequently, a gap 102 is formed between the interior cylindrical surface 100 and the bottom 28. Measured radially, there should be a gap of at least 0.001 inch (0.025 mm) and preferably greater than at least 0.0015 inch (0.038 mm). The gap between the valve body and the stiffening ring should be no more than 0.015 inch (0.381 mm) and preferably no more than 0.007 inch (0.178 mm), measured radially. If the measurements are made diametrically, of course, these values would be doubled.

When the mechanical heart valve 12 is placed in the heart, it will be subject to compressive forces arising from the contraction of the heart muscles. In prior valves, these forces have been resisted by the combined structure of the annular valve body 18 and the stiffening ring 72. Materials under stress deform. It has been necessary, therefore, to design valves with sufficient strength so that, under compressive load, the flexible valve body would not be overly deformed and so that the interior dimensions of the valve body would not compress at the pivots, potentially causing the leaflets to bind.

In the heart valve of our invention, however, compressive forces are initially resisted solely by the stiffening ring 72, which is compressed by such forces into the groove 26. Significant compression of the stiffening ring is acceptable because the resulting change in radial dimension is not transmitted to the annular valve body 18 nor are the pivot recesses 24 displaced inwardly, which might cause binding of the leaflets. On the other hand, as we will explain more fully hereafter, if the pivots and recesses are appropriately tapered, the opening action of the leaflets will cause the valve body 18 to assume a slightly ellipsoid shape. The valve body can assume this shape more readily because these expansive forces are not resisted by the combined structure of the annular valve body 18 and the stiffening ring 72, but only by the annular valve body 18. Because the stiffening ring primarily resists compressive forces while the annular valve body primarily responds to expansive forces, the overall radial thickness of the combined valve body and stiffening ring/sewing ring combination can be made thinner than conventional mechanical heart valves, despite the existence of the gap 102.

Figure 5:
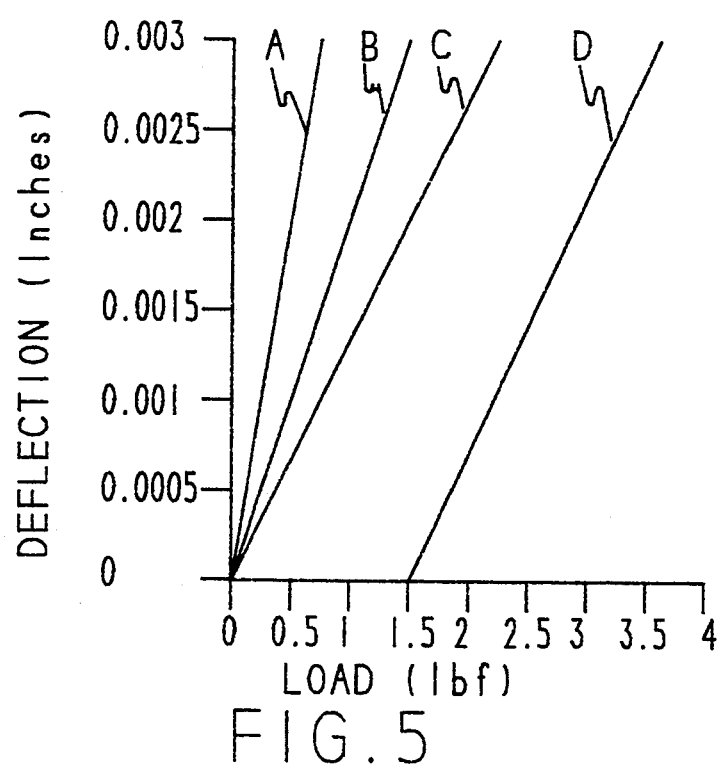
FIG. 5 is a graph of applied load to deflection.
Figure 6:
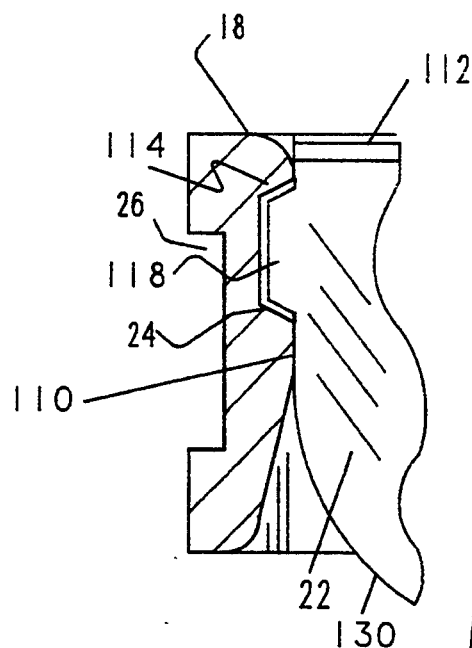
FIG. 6 is a fragmentary view taken partly in cross section along line 6—6 of FIG. 3.

One advantage of our design can be understood by reference to the graph shown in FIG. 5. It is desirable to make the combination of stiffening ring, sewing ring and annular valve body as thin as possible in a radial direction so that the orifice within the annular valve body can be as large as possible. The larger the orifice is, the smaller the hemodynamic energy loss across the valve will be. However, the valve must also resist compression from the muscular contraction of the heart. All materials deform under loads, but if the deformation is excessive, the annular valve body could be pressed against the leaflets or ears, causing the leaflets to stick. At line B in FIG. 5, the interior radial deformation of a typical stiffening ring under compressive load is shown. In other words, the change in inside diameter in response to applied force is shown. At line A, the same measurement for a typical annular valve body is shown. Clearly, the stiffening ring is more resistant to compressive forces than the annular valve body. Moreover, as shown by line C, the combination of the stiffening ring and valve body is even more resistant, being the sum of the resistances of the stiffening ring and the valve body. However, the displacement of the inner most wall, in all three cases, begins essentially at the lowest compressive loads. The interior deflection or diametrical change of dimension of a valve according to our invention is illustrated by line D. Because the stiffening ring is spaced away from the annular valve body, it must first be compressed by a certain amount before any load is transmitted to the annular valve body. Thus there is no deflection of the inside wall of the annular valve body until a certain threshold has been reached (in the illustration, 1.5 lbf). Assuming, as an example, that a heart valve designer had determined that the expected compressive load on the heart valve was 2 lbf and that the acceptable deflection of the inner wall of the annular valve body was 0.002 inches. The thickness of the conventional heart valve, represented by line C, would have to be increased to meet this design criteria. A heart valve according to our invention, on the other hand, would easily meet this criteria. In fact, the radial thickness of the of the stiffening ring or the valve body could be reduced, thus permitting a larger orifice for the same outside diameter of the sewing ring. Of course, the stiffening ring itself will flex more in a valve according to our invention than in a conventional valve, but since this deflection is not transmitted to the interior of the valve body, it has no adverse effect.

The action of the leaflets against the annular valve body also produces an advantage. If tapered stops or recesses are provided, a certain amount of "spring loading" can be obtained from outward deformation of the valve body in response to the opening of the leaflets. We will now explain this feature in greater detail, using FIG. 6.

The valve body 18 has a generally annular configuration with an inner surface 108. The inner surface 108 extends cylindrically throughout most of the valve body interior, except for raised flat surfaces 110 which are generally parallel to one another, extending across chords of the inner surface 108. The valve body 18 is symmetrical about a valve body midplane or center line CL (see FIG. 7), at which plane edges 112 of the leaflets meet when the valve closes. The recesses 24 are formed in the flat surfaces 110 to provide a hinge mounting for the leaflets 20, 22. At least two recesses are required for the mounting of each leaflet, and are located adjacent the diametral edge of that leaflet. Pairs of recesses and leaflets are mirror images about the midplane.

The recess 24 forms a generally triangular shaped opening in flat surface 110 with inclined peripheral side walls 114 so that an inner surface 116 is formed identical in shape but smaller than the opening in flat surface 110. The recesses are enlarged with respect to the mounting ears to provide smooth, low friction operation of the leaflet during opening and closing with a considerable portion of the leaflet travel comprising a translational "floating" which is substantially free of frictional engagement with the recess mating edges. Outward projections or mounting ears 118 extend from flat edge portions 120 of a leaflet. The ears 118, extending toward the interior of recess 24, comprise two opposing halves of a truncated cone separated by planar surfaces. Inwardly tapered peripheral walls form a trapezoid in section. As can be seen with further reference to FIGS. 8 and 9, the surface of the mounting ear is trapezoidal in side view and forms a smooth surface of transition.

Figure 7:
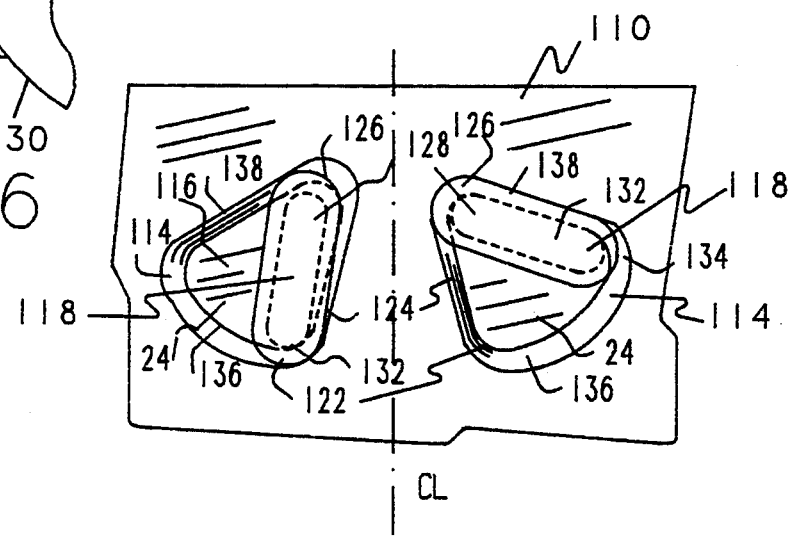
FIG. 7 is a fragmentary plan view of pivot recesses.
Figure 8:
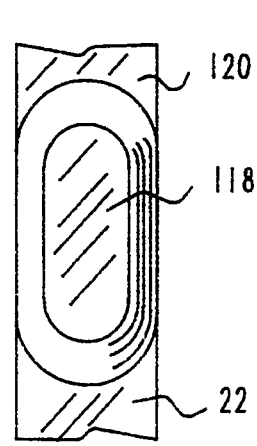
FIG. 8 is a fragmentary top view of a leaflet ear.
Figure 9:
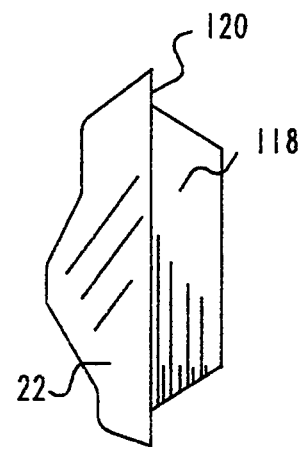
FIG. 9 is a plan view of the ear of FIG. 8.

Referring now to FIG. 7, the leaflets move between open and closed positions in response to blood flow through the valve 12. In the open position shown on the left side of FIG. 7, the mounting ears 118 are seated in a first end portion 122 of recesses 24. Forward flow of blood through the valve forces the tapered walls of the ears 118 against the tapered walls of the recess 24. This is translated into a small radially outwardly directed force which deforms the valve body into a slightly ellipsoid shape. The deformation is halted as the major axis of this ellipsoid reaches the inner dimension of the stiffening ring 72. The combination of the valve body and stiffening ring increases the relative resistance to deformation by such a degree that deformation essentially stops. This prevents the annular valve body 18 from deforming so greatly that the leaflets might disengage. To prevent such an occurrence, the gap between the valve body and the sewing ring, measured radially, should be no more than 0.015 inch (0.381 mm) and preferably no more than 0.007 inch (0.178 mm). At the same time, the slight deformation caused by this action produces a spring-loading effect, which helps to start the closing of the leaflets.

In natural heart valves, the leaflets begin to close as the velocity of flow is reduced, so the leaflets are partially closed before flow reversal. In previous mechanical valves closure did not begin until the flow direction had reversed. This leads to unintentionally high closing volumes which reduce the valve efficiency and to high velocity closures which are noisy and which could result in structural damage. This spring loading will begin the closing motion during flow deceleration, increasing the valve's efficiency and decreasing the leaflets' terminal velocity.

As the cardiac cycle continues, blood begins to flow back through the valve 12 into an adjacent upstream chamber of the heart. The leaflets 20, 22 of the valve 12 close to inhibit back flow. An inner side wall 124 prevents the leaflet 20, 22 from opening completely parallel to centerline CL when the valve 12 is open. The first end portion 122 of the recess 24 is, therefore, further away from the centerline CL than is a pivotal vertex 126 of the recess 24. The pivotal vertex 126 is on the upstream side of the valve 12 when compared to the first end portion 122. As back flow commences, the leaflets 20, 22 move toward the upstream side of the valve 12 and an upstream ear end 128 moves into contact with the pivotal vertex 126 of the recess 24. The upstream ear end 128 is now in rotational sliding contact with the pivotal vertex 126. Because the ears 20, 22 were inclined away from the centerline, the back flow of the blood gives a slight torque to the leaflets 20, 22 and the leaflets begin to pivot around the upstream end 128 of the ears 118. Because the upstream end 128 of the ears 118 is relatively close to the leaflet edge 112, the torque acting on the leaflets 20, 22 is maximized and the leaflets tend to close quickly. Moreover, because the upstream end 128 is constrained in the pivotal vertex 126, the path of an outer semicircular edge 130 of the leaflet is well defined and the leaflets tend to seat against the inner cylindrical surface 108 quickly and accurately.

When the leaflets 20, 22 of the valve 12 are closed as shown in the right half of FIG. 7, the upstream ear end 128 is slightly displaced from the pivotal vertex 126. A downstream ear end 132 is displaced away from a second end 134 in the recess 24. As the pressure of the blood begins to open the leaflet, there is no frictional resistance to the movement to the ear 118 at the downstream end 132. The leaflets 20, 22 will begin to pivot. As the leaflets move from their closed position to their open position, the distal ear end 132 will come in contact with a concave side wall 136 of the recess 24. The upstream end 128 of the ear 118 is now sliding against the inner side wall 124, while the downstream ear end 132 is in generally sliding contact with the concave side wall 136. Normal forces between the downstream ear end 132 and the concave side wall 136 tend to assist the movement of the ear to its open position adjacent inner side wall 124.

Referring now to FIG. 7, recesses 24 include the first and second opposed, generally arcuate end portions 122, 134 respectively and generally arcuate pivotal end portion 126. The first end portion 122 is located spaced from the centerline CL of the prosthesis, the second end portion 134 is located remote from that centerline and above the first end portion 122. The three ends generally form a triangle. The sloping or bevelled, slightly concave side wall 136 extends between the end portions 122, 134. Similar sloping or bevelled but generally linear side walls 124, 138 extend between ends 122 and 126 and between ends 134 and 126, respectively. All of the side walls and ends have an identical slope or bevel with respect of the flat surface 110. The cross-sections of the recesses 24 are generally profiled so as to mate with the profiles of the mounting ears 118, as illustrated in FIG. 7. For further information on these ears and recesses, see U.S. Pat. No. 5,147,390 and U.S. Pat. No. 5,192,313.

The tapered configuration of the ears 118 is also preferred because that shape results in less play over the life of the valve prosthesis, particularly as the valve suffers a certain amount of inevitable wear. Even should noticeable wear occur on certain parts of the conical ears, the increase in lateral play of the leaflet (in directions generally normal to the flat upstream surface) has a potential for being much smaller, compared to leaflet ears of other configurations, such as spherical configurations, for example. The potential for reduced wear was explained in U.S. Pat. No. 4,689,046. As pointed out in that patent, small amounts of wear in the outer surface of hemispherical ears results in a more substantial lateral play of the leaflets than is experienced in the preferred frustro-conical ears. Depending upon the recess contour and the leaflet configuration and design of its mounting, additional advantages may be realized when conical ears are employed over spherical ears in that, when nested in a similarly contoured recess, the conical ears have a potential for establishing a line contact with the bevelled side walls of the recess, whereas spherical ears, if worn unevenly, tend to establish one or more point contacts with their cooperating, similarly configured recesses.

The mating leaflet ears and cooperating recesses of the preferred embodiment are expected to exhibit a very uniform level of wear over the expected life of a patient fitted with the heart valve 12. This is due in part to the configuration of the recesses which allow the leaflet mounting ears 118 to "float" free of significant frictional contact with the recess side walls as the leaflet is moved between open and closed positions. However, even though the leaflet operates with a relatively low friction, the movement of the leaflets is well controlled throughout the life of valve 12 because of the cooperating ears 118 and complementary-shaped recesses 24 in which the ears ride.

Our invention may be embodied in other specific forms by those of skill in the art without departing from the spirit or essential teachings thereof. The foregoing description is intended, therefore, to be illustrative and the scope of our invention is defined by the appended claims.

We claim as our invention:

1. A heart valve prosthesis comprising
   a generally annular valve body configured around an axis and having an inner surface defining a central orifice through which blood flows and an outer surface with a circumferential groove therein, said groove having a bottom surface;
   at least one leaflet proportioned to be pivotally received within said valve body and to move between an open position permitting blood to flow in a downstream direction and a closed position blocking flow of blood in an upstream direction;
   a stiffening ring circumferentially mounted about said annular valve body within said circumferential groove, said stiffening ring having an inner surface facing said bottom surface of said groove, said inner surface being radially spaced away from said bottom surface a distance sufficient to permit resistance to compressive forces and forming a gap there between; and
   a sewing ring mounted on said stiffening ring.

2. The heart valve according to claim 1 wherein said inner surface is spaced away from said bottom surface by an average distance, measured radially, of at least 0.001 inch (0.025 mm).

3. The heart valve according to claim 2 wherein said inner surface is spaced away from said bottom surface by an average distance, measured radially, of not more than 0.015 inch (0.381 mm).

4. The heart valve according to claim 3 wherein said inner surface is spaced away from said bottom surface by an average distance, measured radially, of at least 0.0015 inch (0.038 mm).

5. The heart valve according to claim 4 wherein said inner surface is spaced away from said bottom surface by an average distance, measured radially, of not more than 0.007 inch (0.178 mm).

6. The heart valve according to claim 2 wherein said inner surface is spaced away from said bottom surface by an average distance, measured radially, of at least 0.0015 inch (0.038 mm).

7. The heart valve according to claim 6 wherein said inner surface is spaced away from said bottom surface by an average distance, measured radially, of not more than 0.015 inch (0.381 mm).

8. The heart valve according to claim 1 further comprising
   means for spring-loading said at least one leaflet by deforming said annular valve body radially outwardly.

9. The heart valve according to claim 8 wherein said inner surface is spaced away from said bottom surface by an average distance, measured radially, of at least 0.001 inch (0.025 mm).

10. The heart valve according to claim 9 wherein said inner surface is spaced away from said bottom surface by an average distance, measured radially, of not more than 0.015 inch (0.381 mm).

11. The heart valve according to claim 10 wherein said inner surface is spaced away from said bottom surface by an average distance, measured radially, of at least 0.0015 inch (0.038 mm).

12. The heart valve according to claim 11 wherein said inner surface is spaced away from said bottom surface by an average distance, measured radially, of not more than 0.007 inch (0.178 mm).

13. The heart valve according to claim 9 wherein said inner surface is spaced away from said bottom surface by an average distance, measured radially, of at least 0.0015 inch (0.038 mm).

14. The heart valve according to claim 13 wherein said inner surface is spaced away from said bottom surface by an average distance, measured radially, of not more than 0.015 inch (0.381 mm).

15. The heart valve according to claim 8 wherein said means for spring-loading comprise at least one tapered ear on said leaflet and a correspondingly tapered recess in said annular valve body for receiving said ear.

16. The heart valve according to claim 15 wherein said inner surface is spaced away from said bottom surface by an average distance, measured radially, of at least 0.001 inch (0.025 mm).

17. The heart valve according to claim 16 wherein said inner surface is spaced away from said bottom surface by an average distance, measured radially, of not more than 0.015 inch (0.381 mm).

18. The heart valve according to claim 17 wherein said inner surface is spaced away from said bottom surface by an average distance, measured radially, of at least 0.0015 inch (0.038 mm).

19. The heart valve according to claim 18 wherein said inner surface is spaced away from said bottom surface by an average distance, measured radially, of not more than 0.007 inch (0.178 mm).

20. The heart valve according to claim 16 wherein said inner surface is spaced away from said bottom surface by an average distance, measured radially, of at least 0.0015 inch (0.038 mm).

21. The heart valve according to claim 20 wherein said inner surface is spaced away from said bottom surface by an average distance, measured radially, of not more than 0.015 inch (0.381 mm).

22. The heart valve according to claim 15 wherein said at least one leaflet comprises two leaflets.

23. The heart valve according to claim 22 wherein said inner surface is spaced away from said bottom surface by an average distance, measured radially, of at least 0.001 inch (0.025 mm).

24. The heart valve according to claim 23 wherein said inner surface is spaced away from said bottom surface by an average distance, measured radially, of not more than 0.015 inch (0.381 mm).

25. The heart valve according to claim 24 wherein said inner surface is spaced away from said bottom surface by an average distance measured radially, of at least 0.0015 inch (0.038 mm).

26. The heart valve according to claim 25 wherein said inner surface is spaced away from said bottom surface by an average distance measured radially, of not more than 0.007 inch (0.178 mm).

27. The heart valve according to claim 24 wherein said inner surface is spaced away from said bottom surface by an average distance, measured radially, of at least 0.0015 inch (0.038 mm).

28. The heart valve according to claim 27 wherein said inner surface is spaced away from said bottom surface by an average distance measured radially, of not more than 0.015 inch (0.381 mm).

* * * * *